United States Patent [19]

Kanare et al.

[11] Patent Number: 5,336,255
[45] Date of Patent: Aug. 9, 1994

[54] ELECTRICAL STIMULATION HEAT/COOL PACK

[76] Inventors: Donald M. Kanare, P.O. Box 2933, Alameda, Calif. 94501; Thomas E. Abdenour, 14644 Outrigger, San Leandro, Calif. 94577; Jens Axelgaard, 811 Tumbleweed La., Fallbrook, Calif. 92028

[21] Appl. No.: 3,101
[22] Filed: Jan. 11, 1993
[51] Int. Cl.⁵ .............................. A61N 1/18; A61F 7/00
[52] U.S. Cl. .............................. 607/149; 607/152; 607/153; 607/112; 607/114
[58] Field of Search .................. 128/639–641, 128/644, 399, 402–403, 798, 802–803; 607/96, 104, 108–112, 114–115, 149, 152–153

[56] References Cited

U.S. PATENT DOCUMENTS

| | | |
|---|---|---|
| 4,140,130 | 2/1979 | Storm, III .................. 128/798 |
| 4,576,169 | 3/1986 | Williams .................. 128/403 X |
| 4,708,149 | 11/1987 | Axelgaard .................. 128/798 |
| 4,722,354 | 2/1988 | Axelgaard .................. 128/798 |
| 4,887,614 | 12/1989 | Shirakami et al. ............ 128/798 |
| 5,016,629 | 5/1991 | Kanare .................... 128/379 |

Primary Examiner—Angela D. Sykes
Attorney, Agent, or Firm—Walter A. Hackler

[57] ABSTRACT

An electrical stimulation heat/cool pack includes a nonconductive pouch and straps for positioning and holding the nonconductive pouch against a body part. Flexible conductive fabric patches may be removeably attached, or permanently fixed, to the nonconductive pouch along with lead wires for electrically connecting the fabric patches to a remote pulse generator. An electrically conductive adhesive gel pad is provided for releasably coupling the flexible conductive fabric patch to the body part.

12 Claims, 2 Drawing Sheets

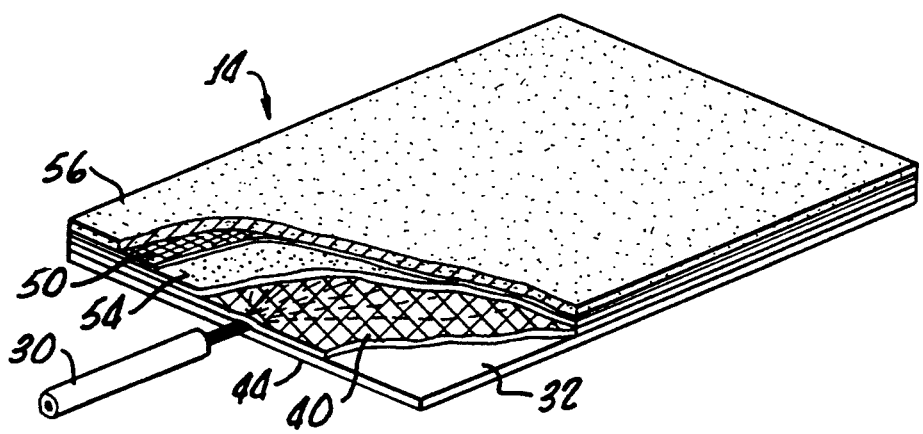
_FIG. 4._
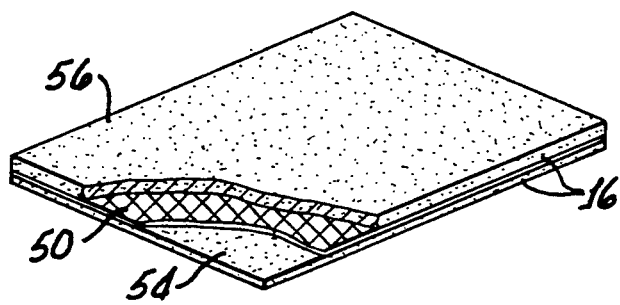
_FIG. 5._
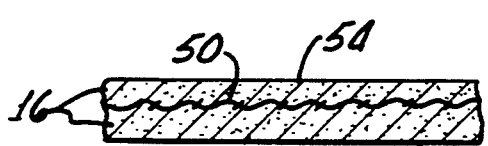
_FIG. 6._
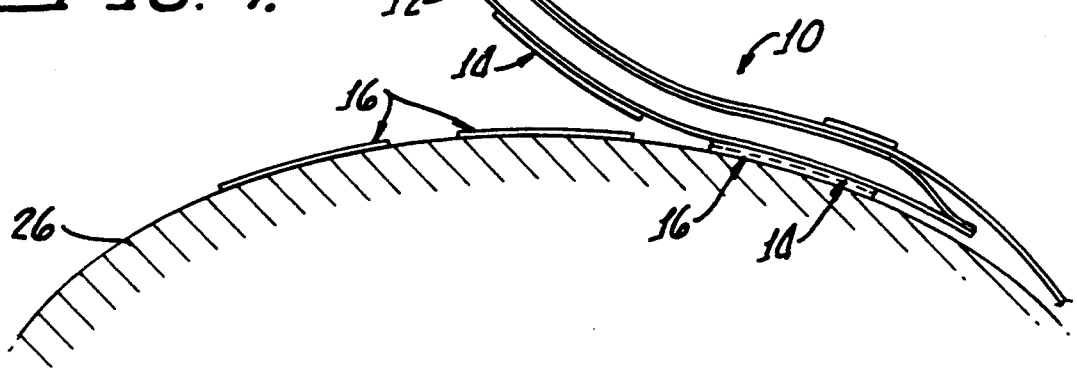
_FIG. 7._

ELECTRICAL STIMULATION HEAT/COOL PACK

The present invention generally relates to a stimulation electrode system in combination with a heat transfer pack useful for both heating or cooling a body and providing electrical impulses to the body.

Transcutaneous electrical nerve stimulation is useful, for example, in post-operative and chronic pain control, while muscle stimulation is useful, for example, in maintenance and development of muscle tissue and has a particularly important function in sports medicine.

The treatment of localized injury or pain which may be caused by torn muscles and connective issues has been therapeutically treated by a heating or cooling of the sprained or strained muscle tissues. Hot and cold thermal packs are used to speed and enhance the healing process, and some treatment regimes may include the alternation of hot and cold applications to stimulate the healing process.

Holders, pouches, bags and the like have been utilized in combination with heating pads, hot water bottles, and other available hot/cold packs to serve as a barrier between the thermal pack and the user's skin.

Thus, the holder of the hot/cold packs provides a barrier which may be used to protect the user's skin from injury. Such a hot or cold body pack is described in U.S. Pat. No. 5,016,629.

Another important treatment for both pain control and muscle tone includes transcutaneous muscle stimulation as hereinabove noted.

Electrodes suitable for use in nerve and muscle stimulation preferably provide a uniform electrical coupling across the skin for electrical interface.

Prior art electrodes have utilized a number of conductive elements, such as carbon impregnated rubber and vinyl, as well as metallic foils.

However, a useful electrode must be flexible in order to accommodate relative movement of the patient's skin therebeneath.

In order to electrically couple the electrode to the skin, prior art devices have utilized many types of conductive electrolytes, both in the form of fluids and gels.

One type of electrode used for temporary application of muscle stimulation includes a flat, smooth contacting surface with a separate conductive cream or gel applied to the skin to electrically couple the electrode thereto. Experience with this system has shown that the cream or gel is messy to use and remove and the electrodes are not suitable for curved body parts. After use, the cream or gel must be cleaned or washed from the skin and electrode.

Another type of electrode most suitable for longer term application of electrical stimulation or monitoring includes a flexible conductive fabric or material.

Typically, this type of electrode includes a woven, knit or mesh material with a gel electrolyte impregnated therein in order to improve electrical conduction within the electrode.

In most instances, this conductive gel is adhesive in nature so that it may perform a dual function by both electrically coupling the electrode to the body and adhering the electrode to the body. A typical electrode of this kind is disclosed in U.S. Pat. No. 4,708,149 and U.S. Pat. No. 4,722,354. These electrodes include a conductive fabric with a flexible conductive adhesive disposed on one side of the conductive fabric for adhering the flexible transcutaneous electrical nerve and/or muscle stimulation electrode to the skin of a patient.

While this type of electrode is effective, a great number of electrodes may be required to provide long term treatment for certain injuries, such as those incurred in sports.

Since most of the known electrodes are disposable in nature and useful for only relatively short periods of time, due to removal for body hygiene, a considerable expense may be anticipated in the treatment of a patient.

The present invention is directed to an electrical stimulation heat/cold pack in which the electrical distribution portion of the electrode and heat/cold pack is reusable and, in fact, washable. Importantly, the heat/cold pack in accordance with the present invention is configured for both heating and cooling applications. In combination therewith and in accordance with the present invention, a separate adhesive electrically conductive pad is used to couple the "dry" heat/cold pack to the skin. Thus, only an expendable gel pad material need be disposable throughout the treatment of the patient. In addition, one embodiment of the present invention also enables the use of a plurality of electrodes, which may be of diverse size, in combination with a support member with spacing between electrodes selected and adjusted as may be preferred, depending on the use and application of the system.

SUMMARY OF THE INVENTION

An electrical stimulation body pack, in accordance with the present invention, generally includes a flexible pouch including means for containing a heat transfer medium and means for positioning and holding the flexible pouch against a body part.

A flexible, electrically conductive electrode, attached to the nonconductive pouch includes a lead wire for electrically connecting the patch to an electrical stimulator. More particularly, a plurality of flexible conductive electrodes may be attached to the pouch material, each being separately connected to electrical lead wires. The pouch and the flexible conductive electrodes may be formed from a washable material, thus enabling repeated reuse of this equipment in accordance with the present invention. In addition, the pouch may include a loop material and the electrodes may include hook means for enabling the electrodes to be disposed on either side of the pouch and at various positions.

The electrode of the present invention may include a separate conductive patch and an electrically conductive gel for releasably coupling the flexible conductive fabric patch to the body part with the electrically conductive gel being removable from the flexible conductive fabric patch. Thus, the conductive gel in accordance with the present invention is a separate and disposable item.

Since the conductive gel is not disposed within interstices of the fabric and bound to the fabric, a clean separation of the patch from the conductive gel is effected. In addition, because the gel has dimensional integrity, it cleanly separates from the body part. Hence, no separate cleaning or washing of the body part is necessary as is required by prior art devices.

In another embodiment of the present invention, the flexible conductive fabric patch, or patches, may be sewn to the pouch, and the lead wire includes a plurality of electrically conductive strands with the latter sewn to the flexible conductive fabric patch. This embodiment may be preferred when the pack is intended to be used solely for cooling applications only or solely for heating applications.

To facilitate coupling of the patches to an electrical stimulator a separate connector or snap may be used to join the lead wire to the output line or lines from the electrical stimulator.

Alternatively, the conductive fabric patch may be glued to the nonconductive fabric and the lead wire glued to the conductive fabric patch.

BRIEF DESCRIPTION OF THE DRAWINGS

The advantages and features of the present invention will be better understood by the following description when considered in conjunction with the accompanying drawings in which:

FIG. 4 is a cross-sectional representation of conductive patch shown in FIG. 1;

FIG. 5 is a perspective view, partially broken away, of a gel pad in accordance with the present invention; and FIG. 6 is a figure showing release of the conductive fabric patch from the skin of the user.

DETAILED DESCRIPTION

Figure 3:
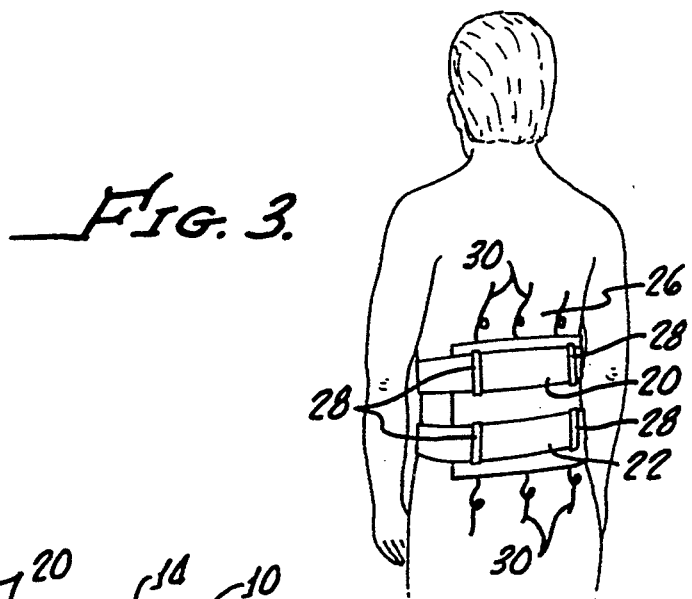
FIG. 3 is a perspective view of the embodiment shown in FIG. 1 as it may be disposed on a body part.

Turning now to FIGS. 1-4, there is shown an electrical stimulation heat/cool pack 10 which generally includes a fabric pouch 12 formed from a nonconductive material and flexible conductive electrode patches 14 attached to the pouch 12. Straps 20, 22 provide a means for positioning and holding the nonconductive fabric 12 against a body part, such as a back 26, as shown in FIG. 3. Loops 26, 28 disposed on opposite sides 12a, 12b of the pouch 12 enable either side 12a, 12b to be compressed against a body part depending on whether a hot or cold application is desired as will be discussed hereinafter in greater detail.

The pouch 12 construction, as well as the straps 20, 22 may be made in accordance with the teachings of U.S. Pat. No. 5,016,629, which is incorporated herein by this specific reference thereto.

A heat transfer medium 29 may include a plurality of individual packets or one packet suitable for retaining heat or cold and be comprised of any suitable material as is well known in the art.

Both sides 12a, 12b of the pouch 12 are preferably formed from a velvet loop material. This enables the patches 14 to be positioned at any selected location on either side 12a, 12b of the pouch 12 by means of hooks 30, see FIG. 4.

When the patches 14 are disposed on one side 12a, the loops 26 are utilized with the straps 20, 22 to secure the heat/cold pack 10 against a body part. Alternatively, when the patches 14 are disposed on the other side 12b of the pouch 12, the loops 26 are utilized with the straps 20, 22 to secure the heat/cool pack 10 against a body part.

For use with a heat transfer medium 29, that has been cooled, a thin liner 32 is disposed under the velvet loop material on side 12a of the pouch 12. This thin layer 32 may be a plastic material in order to act as a moisture barrier for preventing condensation on the cooled heat transfer medium from passing through the velvet loop material and in the patches 14.

The opposite side 12b of the pouch 12 is utilized for heat application, ie when the heat transfer medium 29 is heated. In order to prevent skin burn, an insulated layer 34 is provided under the velvet loop material on side 12b of the pouch 12.

Thus the present invention is useable as both an ice pack stimulator as well as a heat pack stimulator with the repositioning of the patches 14 on sides 12a and 12b of the pouch 12.

Figure 1:
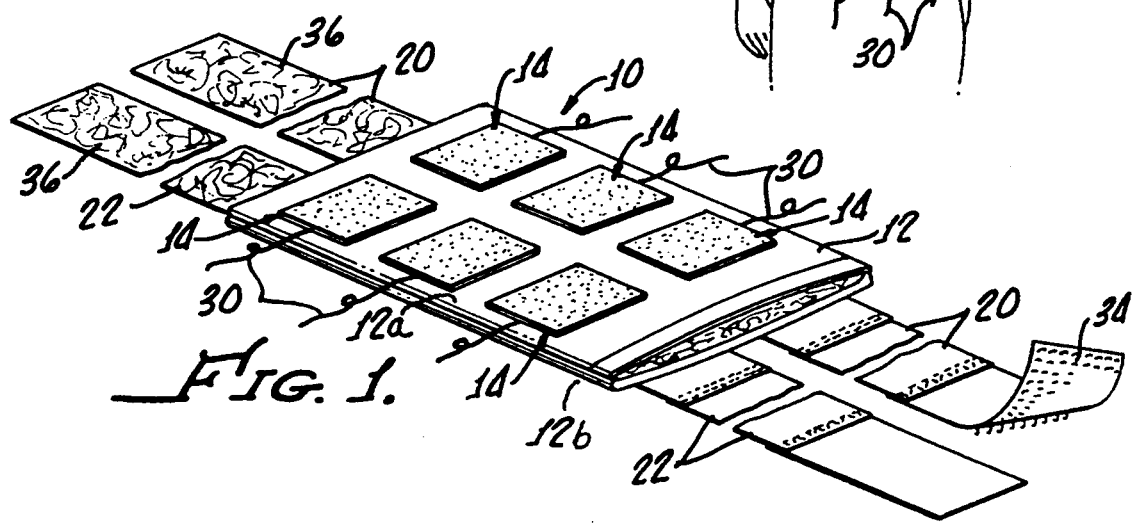
FIG. 1 is a perspective view of an electrical stimulation heat/cool pack in accordance with the present invention.
Figure 2:
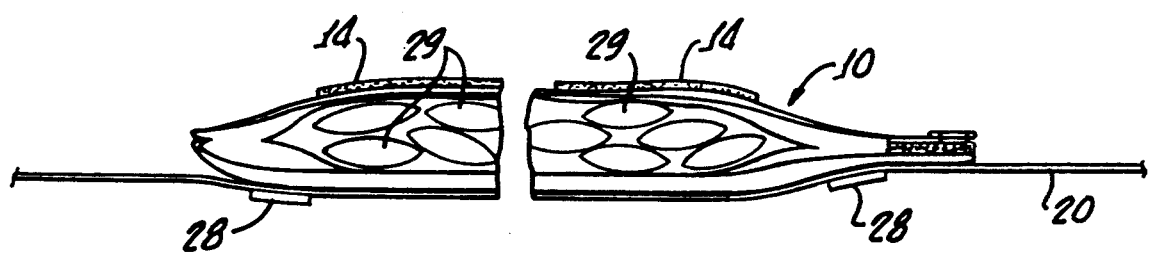
FIG. 2 is a cross-sectional view of the electrical stimulation heat/cool pack shown in FIG. 1.

While a plurality of conductive fabric patches are shown in FIGS. 1 and 2, a single patch may be utilized depending upon the circumstances of treatment. The array of patches shown in FIG. 1 is only representative in nature. However, it is important to note that the fixing of the conductive fabric patches 14 to the nonconductive fabric 12, via the velvet loop material and the hook 30, overcomes the problem associated with using multiple sets of electrodes. The use of loop material and hooks 30 enables easy position changes of the patches with respect to each other and the pouch 12.

When the pouch is to be used for the application of, for example, only a cooled medium or only a heated medium, it may be preferable that the patches 14 may be fixed to the pouch 12 by other suitable bonding methods, such as by adhesive or by sewing.

A spaced apart, fixed positioning of the electrode eliminates the cumbersome and unwieldy necessity of separate attachment of electrodes to a body. In addition, with single or smaller sets of electrodes, migration during prolonged stimulation may occur and thus cause difficulty in ensuring consistent placement of the electrodes with respect to one another.

More particularly, the nonconductive fabric pouch 12, in accordance with the present invention, may be formed from any suitable material which is preferably machine washable. The function of the nonconductive pouch 12 is to provide a support for the conductive patches 14 and prevent any unwanted electrical communication between the electrodes or contact with the electrodes when the patches are placed in contact with the body, and simultaneous transfer heat or cold to the body. Also important is the function of the pouch liner 32 in providing a moisture barrier and insulation 34 in preventing skin burn.

The liner, or moisture barrier layer 32, provided over the nonconductive fabric 12, prevents the entry of moisture as may be present in the environment of use as hereinabove discussed. Any suitable barrier such as polyurethane may be utilized.

The straps 20, 22, which are preferably formed of an elastic material, are preferably separate from the pouch 12 in order to facilitate the reversal of the pack 10, however they may be sewn to the pouch 12 in certain applications. As shown, the straps 20, 22 may be secured on a body by means o f a hook 36 and pile 38 arrangement, as is well known in the art. The purpose of the straps 20, 22 is to ensure contact of the patches 14 with the gel 16 over a long duration of time and insure good thermal transfer between the body and the heat transfer medium 29 in the pouch 12. Further, the straps 20, 22 provide additional pressure for insuring electrical contact between the conductive patches 14 and the body part through the gel 16.

In addition, the straps 20, 22 provide a means for compressing the body part as may be advantageous for use with sports injuries, for example. Also when properly sized, such compression straps 20, 22 may be useful for support of a body part, such as, for example, a low back support. (See FIG. 3)

In muscle stimulation applications, the electrodes have a tendency to migrate and hence prior art utilization of multiple separate electrodes requires constant monitoring in order to insure proper placement of the electrodes. The present invention overcomes this disadvantage by maintaining proper relative placement of multiple electrodes.

Turning to FIG. 4 and 5, the conductive fabric patches 14 may be formed from any suitable flexible, conductive fabric or material, but preferably are formed from a stretchable conductive material such as that described in U.S. Pat. Nos. 4,708,149 and 4,722,354, which are incorporated herewith in toto by specific reference thereto.

Conductivity of the fabric patches is provided by individual conductive fibers 40 (see FIG. 4). A particularly suitable fiber is one manufactured by Bekaert of West Germany. This fiber, a blend of 20% 316 stainless steel and 80% polyester, can be latch-needle, honeycomb knitted to a density of about 3.5 lbs. per sq. yd., producing a conductive, double-stretch knit. Naturally, other conductive fabrics may be utilized in the present invention.

Because the patches 14 are also machine washable, along with the pouch 12 and the straps 20, 22, the entire pouch 12 may be cleaned and reused, without disturbing the placement of the patches 14 on the pouch 12, which provides favorable cost benefits to the patient undergoing long term treatment as well as insuring proper electrode placement throughout the long term treatment.

As also shown in FIG. 4, a lead wire 42 comprises a plurality of connective strands 44 which may be of stainless steel. The strands may be sewn in place onto the conductive patches 14 and may be fanned if necessary to provide more intimate contact with the fibers 40. The compression, upon sewing of the strands 44, to the conductive patches 14 provides sufficient electrical contact therebetween to enable electrical impulses to be distributed over the entire area of patch 14. Each of the lead wires 42 are electrically connected to a remotely disposed electrical stimulator (not shown).

The sewing of the lead wire is facilitated by utilizing a large plurality of strands, such as for example, about 1000 to about 1200 strands of 8 micron stainless steel. Alternatively, the strands 44 may be adhered to the conductive patches with a suitable conductive glue thereby enabling the assembly of the electrode without any sewing steps. It should also be appreciated that any suitable electrical connection may be utilized in order to deliver an electrical charge to the individual electrode patches 14.

FIG. 5 shows a disposable gel pad 56 in accordance with the present invention, which should be formed in a sufficient size to cover the patches 14 but not overlap with adjacent fabric patches.

A suitable conductive gel adhesive 56 is manufactured by Valleylab, Inc. of Boulder, Color., under the name "Polyhesive ®". The pads 56 may be formed by molding a liquid into a gel-like material.

In accordance with the present invention, the gel pad may have an overall thickness of between about 0.020 inches and about 0.100 inches.

A separate gel importantly enables the patches 14 and pouch 12 to be removed from the gel as shown in FIG. 6, thereby facilitating reuse of the patches 14 and pouch 12 without the necessity of scraping or removing gel therefrom. In addition, in prolonged use, as hereinabove mentioned, the patches 14 and support pouch 12 may be washed as necessary between use.

Although there has been hereinabove described a specific arrangement of an electrically stimulated heat/-cool pack with moveable electrode patches in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. An electrical stimulation body pack comprising:
   a flexible electrically non-conductive pouch including means for containing a heat transfer medium, said flexible pouch being formed from a nonelectrically conductive fabric, said pouch including a first surface having moisture barrier means for separating a chilled heat transfer medium from a contacted body and a second surface having insulation means for separating a heated heat transfer medium from a contacted body in order to prevent skin burn;
   means for positioning and compressing either of the first and second surfaces of said flexible pouch against a body part;
   a flexible electrical nerve and muscle stimulation electrode attached to the flexible pouch at a position enabling direct contact between the stimulation electrode and the body part when either of the first and second surfaces of said flexible pouch is compressed against the body part; and
   a lead wire electrically connected to the flexible nerve and muscle stimulation electrode.

2. The electrical stimulation body pack according to claim 1 wherein both pouch surfaces include a loop material and said flexible electrical stimulation electrode comprises hook means for providing placement of the electrode at various positions on both pouch surfaces.

3. An electrical stimulation body pack comprising:
   a flexible electrically non-conductive pouch including means for containing a heat transfer medium, said flexible pouch being formed from a nonelectrically conductive fabric, said pouch including a first surface having moisture barrier means for separating a chilled heat transfer medium from a contacted body and a second surface having insulation means for separating a heated heat transfer medium from a contacted body in order to prevent skin burn;
   means for positioning and compressing either of the first and second surfaces of said flexible pouch against a body part;
   a flexible electrical nerve and muscle stimulation electrode attached to the flexible pouch;
   a lead wire electrically connected to the flexible electrical nerve and muscle stimulation electrode; and
   electrically conductive gel means for releasably coupling the flexible electrical nerve and muscle stimulation electrode to said body part, said electrically conductive gel means being removable from said flexible pouch.

4. The electrical stimulation body pack according to claim 3 wherein both pouch surfaces include a loop material and said flexible electrode comprises hook means for enabling placement of the patch at various positions on both surfaces of the pouch.

5. The electrical stimulation body pack according to claim 4 wherein said means for positioning and compressing said flexible pouch against a body part comprises at least one loop attached to one side of the flexible pouch and a strap sized for passing through said loop and around the body part.

6. The electrical stimulation body pack according to claim 3 comprising a plurality of flexible electrodes attached to said pouch in a spaced apart array with each electrode having a separate lead wire attached thereto.

7. The electrical stimulation body pack according to claim 3 wherein the pouch and the flexible electrode attached thereto are washable.

8. An electrical stimulation body pack system comprising:
a flexible electrically non-conductive pouch including means for containing a heat transfer medium, said flexible pouch being formed from a nonelectrically conductive fabric, said pouch including a first surface having moisture barrier means for separating a chilled heat transfer means from a contacted body and a second surface having insulation means for separating a heating heat transfer medium from a contacted body in order to prevent skin burn;
means for positioning and compressing either of the first and second surfaces of said flexible pouch against a body part;
a plurality of flexible electrical nerve and muscle stimulation electrodes attached to the flexible pouch at a position enabling direct contact between the electrodes and the body part when either of the first and second surfaces of said flexible pouch is compressed against the body part;
a lead wire electrically connected to each electrode; and
electrically conductive gel means for releasably coupling the flexible electrodes to said body part, said electrically conductive gel means being removable from said flexible pouch.

9. The electrical stimulation body pack according to claim 8 wherein both pouch surfaces include a loop material and said plurality of flexible electrodes contains hook means for positioning the electrodes at various locations on both sides of said pouch.

10. The electrical stimulation body pack system according to claim 9 comprising said plurality of flexible electrodes attached to said nonconductive fabric in a spaced apart array with each electrode having a separate lead wire attached thereto.

11. An electrical stimulation body pack comprising:
a flexible electrically non-conductive pouch including means for containing a heat transfer medium, said flexible pouch being formed from a nonelectrically conductive fabric, said pouch including one surface having moisture barrier means for separating a chilled heat transfer medium from a contacted body and another surface having insulation means for separating a heating heat transfer medium from a contacted body in order to prevent skin burn;
means for positioning and compressing said flexible pouch against a body part;
a flexible electrical nerve and muscle stimulation electrodes attached to the flexible pouch;
a lead wire electrically connected to the flexible electrical nerve and muscle stimulation electrode; and
means for providing moveable placement of the electrode at various positions on both pouch surfaces.

12. The electrical stimulation body pack according to claim 11 wherein said means for providing placement comprises a loop material on both pouch surfaces and a hook material disposed on said flexible electrical nerve and muscle stimulation electrode.

* * * * *